United States Patent [19]

Robertson

[11] Patent Number: 5,019,032

[45] Date of Patent: May 28, 1991

[54] REFINED SUSPENSION PROCEDURE WITH IMPLEMENT FOR TREATING FEMALE STRESS INCONTINENCE

[76] Inventor: Jack R. Robertson, 1430 E. Main St., Suite 202, Santa Maria, Calif. 93454

[21] Appl. No.: 503,788

[22] Filed: Apr. 3, 1990

[51] Int. Cl.$^5$ ............................................. A61B 17/00
[52] U.S. Cl. ..................................... 600/29; 128/898; 604/49
[58] Field of Search ....................... 128/898, DIG. 25; 600/30, 29; 604/49, 264

[56] References Cited

U.S. PATENT DOCUMENTS

| | | |
|---|---|---|
| 3,640,281 | 2/1972 | Robertson . |
| 3,656,486 | 4/1986 | Robertson ........................... 606/108 |
| 3,709,214 | 1/1973 | Robertson ............................. 128/4 |
| 4,172,458 | 10/1979 | Peregra .............................. 606/144 |
| 4,938,760 | 7/1990 | Burton et al. ......................... 606/29 |

OTHER PUBLICATIONS

Robertson, R. Jackson, "Instruments and Methods", Obstetrics and Gynecology, vol. 41, No. 4, Apr. 1973, pp. 624–627.
Gittes, Ruben F., "No-Incision Pubovaginal Suspension for Stress Incontinence", J. of Urology, vol. 138, Sep. 1987, pp. 568–570.
Stamey, Thomas A., "Endoscopic Suspension of the Vesical Neck for Urinary Incontinence", Surgery, Gynecology & Obstetrics, vol. 136, pp. 547–554, Apr. 1973.
Mason, Tate J. et al, "Suprapubic Endoscopic Evaluation of Vesical Neck Suspension Procedures", J. Urology, vol. 6, No. 2, pp. 233–234, Aug. 1975.

Primary Examiner—Stephen C. Pellegrino
Assistant Examiner—Gary Jackson
Attorney, Agent, or Firm—Ashen Martin Seldon Lippman & Scillieri

[57] ABSTRACT

The incision-free pubovaginal suspension due to Gittes and Loughlin is improved by simultaneous gas obturation and visual monitoring using a suprapubic endoscope, inserted with the aid of a urethral trocar. It is further improved by simultaneous manipulation of the urethra, bladder and other tissues by the trocar, to optimize alignment for the Gittes procedures. The trocar, and procedure for its use, are refinements of the present inventor's earlier apparatuses and procedures for suprapubic cystostomy with endoscopy, and for gas obturation.

19 Claims, 9 Drawing Sheets

REFINED SUSPENSION PROCEDURE WITH IMPLEMENT FOR TREATING FEMALE STRESS INCONTINENCE

BACKGROUND

1. Field of the Invention

This invention relates generally to medical procedures and apparatus; and more particularly to refinement of such procedures and apparatus for treating stress incontinence in women by pubovaginal suspension without surgery.

2. Prior Art

Ruben F. Gittes and Kevin R. Loughlin have introduced "a modified needle suspension for urinary incontinence that eliminates all incisions." 138 *The Journal of Urology* 568-70 (1987). In their method, as described in an abstract:

"The anterior vaginal wall is suspended from the rectus fascia with 2 heavy nonabsorbable monofilament mattress sutures. The sutures pass down through and back up through the full thickness of the vaginal wall, and are tied suprapubically to bury the knot into the fat in the suprapubic puncture site . . . [M]onofilament mattress sutures that are tied under tension to include the outside abdominal skin will cut through the skin, and become internalized and accepted without any residual inflammation if the knot is buried initially. . . ."

The Gittes and Loughlin procedure evidently provides significant benefits for patients. As also pointed out in the abstract, this procedure:

"makes routine use of outpatient surgery and allows for the use of local anesthesia only in selected patients. At 2½ years the continence rate in the first 38 patients exceeded 87 percent. There were no failures among the last 14 patients after the technique was modified to include an extra full thickness pass of the mattress suture through the vaginal wall. There have been no significant complications."

Without detracting in the least from these potential benefits, it is important to recognize significant limitations in the reported procedure. First, it calls for significant manual dexterity, as well as a visualization capacity approaching the clairvoyant, on the part of the physician:

"A special long mattress-type needle is needed. . . . A small puncture is made . . . into the suprapubic fat pad. . . . The long needle is popped through the rectus fascia and the anteriorly deflected tip is advanced carefully down the posterior aspect of the pubic bone. At the same time, the operator's second hand elevates the anterior vaginal wall lateral to the Foley balloon, thus, just lateral to the bladder neck. Wiggling the needle from above and directing it toward the fingertip by rocking forward the suprapubic portion of the needle shaft avoids a false passage into the bladder or past the lateral vaginal wall. While controlling the tip of the needle with the tip of the finger, the operator examines the tented-up vaginal wall to make sure it is not too medial or lateral, and then the tip is popped through the wall and then forward through the introitus." Id. at 568.

With dexterity and experience, and great care, this procedure undoubtedly can be performed reliably. None of these characteristics, however, can be guaranteed, as Gittes and Loughlin in effect concede:

"Before the suspending sutures are tied down, cystourethroscopy must be done to rule out damage to the bladder wall by the sutures and to place a percutaneous suprapubic [cystostomy] under endoscopic control. The 70-degree telescope allows for close inspection of the bladder wall just inside the bladder neck. If any part of either suture is [seen], either perforating the bladder or even coursing submucosally, that arm of the suture is identified by traction, pulled out into the vagina and replaced upward with a new pass of the mattress needle. In difficult cases, as in bladders widely fixed anteriorly by the Burch modification of the Marshall-Marchetti operation, the passage of the needle can be monitored continuously endoscopically with the 120-degree telescope."

Although Gittes and Loughlin go on to recommend using a suprapubic "puncture" later for placement of a "suprapubic tube of the trocar variety"—for postprocedure drainage—they clearly do not use that puncture for placement of a viewing device for the monitoring step.

From their discussion it is evident that they instead insert an endoscope through the urethra. Their suprapubic drain is installed in a puncture made from the outside while watching the anterior bladder wall from within. That procedure is only a slight improvement on the conventional method, which employs a large trocar inserted suprapubically from above, blind—that is, puncturing the abdominal wall and bladder from the exterior, without any guidance.

The latter method is extremely dangerous and in fact potentially lethal—especially if the patient's anatomy is abnormal, as for example can occur as a result of previous surgery, leaving, e.g., the patient's bowel ventral to the bladder. The improvement gained by the procedure of Gittes and Loughlin is only slight, because watching the anterior bladder wall from within the bladder affords only a fairly rough view of the entry point, and of the bladder configuration and position relative to the abdomen.

The methods described by Gittes and Loughlin are derived from a technique introduced in 1973 by T. A. Stamey, 136 *Surg., Gynec. & Obst.* 547. An early modification by J. T. Mason and R. M. Soderstrom, 6 *Urology* 233 (1975) provided for suprapubic monitoring of needle placement, by means of a rigid cystoscope inserted through a Foley catheter that had been modified for the purpose.

In my opinion, although I have seen nothing in the prior art to support my opinion, that approach should be considered a major improvement. The reason is that using a urethroscope—whether it be a 70-degree or 120-degree instrument—to monitor the needle passage has important drawbacks, as follows.

The area of greatest concern with respect to inadvertent puncture of the vesical wall is the neck of the bladder, for the very reason that the neck is the portion to be elevated, and is immediately adjacent to the vaginal wall—the target of the needles. In other words, it is in this region that the needles must be brought closest; but this is precisely the spot at which the 'scope itself is introduced. The urethroscope is not only immediately adjacent to the neck of the bladder, but also mechanically coupled to the neck of the bladder in a somewhat complicated and unpredictable way.

Hence the practitioner is faced with difficult demands, to say the least, upon dexterity. The objective is to somehow position the urethroscope for best viewing of the immediately adjacent bladder neck, without actively making matters worse by inadvertently pushing the neck itself toward the advancing needle tip.

In many cases these two constraints seem to be mutually inconsistent. Yet Gittes and Loughlin evidenced no appreciation in their 1987 paper for the advance introduced long earlier by Mason and Soderstrom.

Very recently, however, Loughlin has proposed, 142 *J. Urology* 1532 (1989), to update the Mason and Soderstrom modification. (Loughlin's work is not deemed to be prior art with respect to the present document.) Loughlin now substitutes a flexible ureteroscope for the cystoscope, thereby facilitating continuous observation of the bladder wall and neck during passage of the needles. Still, neither Mason and Soderstrom nor Loughlin has offered anything to mitigate the hazards of introducing the viewing device by a blind puncture.

In another area of prior practice, the present inventor some twenty years ago introduced certain procedures and instrumentation for introducing suprapubic catheters without the potentially lethal use of a large trocar in blind insertion. See U.S. Pat. Nos. 3,640,281 and 3,656,486 (both filed 1970); and "Suprapubic Cystostomy with Endoscopy" 41 *Obstetrics-Gynecology* 624-27 (1973).

The system there described is not in prevalent use today, and Gittes and Loughlin make no reference to it. It provides a trocar that is inserted through the urethra, into the bladder, and against the bladder lining and abdominal wall from within; the resulting acute bulge at the exterior of the patient's abdomen is then used by the physician to identify the proper point for a small puncture. The puncture itself is preferably made from the exterior, against the tip of the trocar that is within.

The trocar is then preferably passed through that puncture outward, from within the bladder, and attached outside the body to a catheter or other instrument. Alternatively the trocar need not be actually passed out from the abdomen but can be attached to the catheter or other instrument while lying just within the puncture.

The trocar motion is then reversed to draw the trocar and external instrument through the puncture and into the bladder. Thereupon the trocar can be forthwith disconnected and withdrawn from the urethra, or can be temporarily kept in place for other purposes such as inflation of the bladder.

To facilitate connection and later disconnection of the trocar and the catheter or other instrument, the trocar was fashioned with either a hook, in a lateral recess near its end, or an aligning socket in its tip.

The present inventor also introduced a method and apparatus for facilitating endoscopy through obturation by means of gas—described in U.S. Pat. No. 3,709,214 (filed 1971). The system there described involves placing a gas-obturating endoscope into bodily cavities or organs such as the bladder; and particularly in the case of the bladder involves placement through the urethra.

Gas obturation provides less trauma than mechanical obturation, less cumbersomeness and discomfort than liquid inflation, and a clearer view than either. This system is in somewhat greater use modernly, but also not mentioned by Gittes and Loughlin—or even in Loughlin's most recent paper reintroducing suprapubic viewing.

SUMMARY OF THE DISCLOSURE

Before formally summarizing my present invention, I shall introduce an important consideration which I have only just suggested in an earlier section of the document. None of the prior-art writers—and not even Loughlin in his most recent paper discussed above—evidences any appreciation of this matter.

As I have indicated, a relatively undesirable technique is to monitor suture placement by a viewing instrument (such as the Gittes and Loughlin urethroscope) that is immediately adjacent to, and in fact mechanically coupled to, the most critical wall region. That technique can actively misposition that critical wall region.

A relatively more desirable technique is to monitor placement by an instrument (such as the Mason and Soderstrom suprapubic cystoscope) that is independent of the critical region. In the latter technique, the manipulations needed for good viewing do not interfere with the position of the bladder neck. To put it in another way, the suprapubic viewing technique is at least passive with respect to positioning of the bladder neck: the technique itself does not actively misposition the bladder neck.

What is far preferable, however, is to actively position the bladder neck for optimum results. More specifically, in my procedure—to be described below—the practitioner can readily draw the neck of the bladder away from the advancing needle tip, thereby minimizing the chance of inadvertent puncture. Further, my procedure for the first time combines in the suprapubic suspension method—without compromising any desirable features of that technique—steps to prevent the hazard of blind puncture.

In addition, preferred embodiments of my procedure also avoid discomfort and procedural protraction required for repetitive filling and emptying of the bladder with liquid; and afford a better view of the bladder wall and thus greater ease and certainty of the basic technique.

With this general introduction in mind, I shall now offer a more formal definition of my present invention. It is a procedure for treating incontinence in a woman, comprising the steps of:
(1) inserting a urethral trocar into the woman's bladder and therethrough to press outward firmly against the woman's abdominal wall, so as to be perceptible from the exterior of the woman's body;
(2) then, with the exteriorly perceptible trocar as a guide, making a suprapubic incision in the woman's abdominal wall and bladder to gain access to a tip of the trocar;
(3) then using the tip of the trocar directly or indirectly to guide a tip of a viewing device through the suprapubic incision and into the woman's bladder; and
(4) then installing sutures between the woman's rectus fascia and vagina, by means of a needle inserted through the woman's abdomen and into the woman's vagina;

(5) substantially during the suture-installing step, monitoring the interior of the bladder through the viewing device to avoid placement of sutures in the bladder wall—so that the viewing device is remote from the neck of the bladder, where inadvertent placement of sutures is particularly likely; and (6) substantially during the suture-installing and monitoring steps, maneuvering the trocar or the viewing device, or both, to manipulate tissues of the woman's bladder, urethra, or abdominal wall, or combinations of any of these tissues, to facilitate accurate placement of the sutures, particularly avoiding the bladder and urethra.

The foregoing may define my invention in its broadest or most general form. Even without going further, in my invention as thus described the critical bladder-urethra junction region is actively manipulated away from the needles. Furthermore, a clear view of that region is provided, the hazards of a blind puncture in installing a suprapubic drain and viewing device are essentially prevented, and each of these advantages is obtained without compromising any of the others or compromising the basic technique.

As will be appreciated, however, I prefer to practice my invention with certain further steps, substeps, or characteristics to obtain the greatest enjoyment of the benefits of the invention. Thus the following paragraphs describe and briefly discuss preferred embodiments of my invention, incorporating such additional features.

Most or all of these preferred embodiments are mutually compatible—that is, they can be used together if desired. In fact, as will be seen, certain of the preferred embodiments as defined are somewhat overlapping with respect to others.

In a first preferred embodiment of my invention, the tip-using step (that is to say, the step numbered "3" above) comprises the substeps of: (a) employing the tip of the trocar directly or indirectly to guide an end of a catheter through the suprapubic incision into the woman's bladder; and (b) then inserting the tip of the viewing device through the catheter into the woman's bladder.

Moreover, I prefer to use a catheter that has near its end a balloon. When this is the case, the "employing" substep just mentioned includes guiding the end of the balloon, together with the end of the catheter, through the suprapubic incision into the woman's bladder, and then inflating the balloon to anchor the end of the catheter within the bladder.

In a second preferred embodiment of my invention, the tip-using step comprises the substeps of: (a) mating the tip of the viewing device or of an intermediary appliance with the tip of the trocar; and (b) then moving the tip of the viewing device or appliance, while it is mated with the tip of the trocar, inward through the incision and into the woman's bladder.

In a third preferred embodiment of my invention, the trocar-tip-using step (as before, step "3" above) comprises: (a) passing the trocar tip outward through the suprapubic incision; (b) then mating the tip of an viewing device or of an intermediary appliance with the tip of the trocar; and (c) then moving the tip of the viewing device or appliance, together with the tip of the trocar, inward through the incision and into the woman's bladder.

By comparison of the first three preferred embodiments, which have been introduced above, it will be appreciated that the trocar tip need not be actually passed outward through the incision, out of the patient's body, to be used in guiding a catheter into the bladder (as in the first preferred embodiment mentioned above) or in mating the tip of the viewer or appliance with the trocar tip and moving the tips together into the bladder (as in the second preferred embodiment mentioned above). In other words, the first and second embodiments may be performed, if preferred, with the tip of the trocar remaining just within the incision.

A fourth preferred embodiment includes another step, performed before the inserting step—namely, making or obtaining a urethral trocar that bears visible graduations along at least part of its length. In this fourth preferred embodiment, the trocar-maneuvering step comprises referring to the graduations as they appear at the woman's perineum.

In a fifth preferred embodiment of my invention, the monitoring step comprises inflating the bladder with gas.

In a sixth preferred embodiment, the installing and monitoring steps comprise repetitive performance of this sequence of substeps: (a) placing a suture; (b) then inflating the bladder with gas to facilitate observation of the bladder wall; (c) then observing the bladder wall to determine whether the suture just placed is visible therein; and (d) then deflating the bladder.

A seventh preferred embodiment includes another step, performed before the inserting step—namely, making or obtaining a urethral trocar with a recess at its tip and a generally peripheral ridge around the recess. In this seventh embodiment, the incision-making step comprises pressing a sharp object through the abdominal wall and bladder, and toward and into the recess.

By comparison of the fourth and seventh embodiments discussed above, it will be appreciated that the trocar may be formed to define both the recess and the graduations, and both features can be employed as described above. In addition, most of the preferred embodiments described above are advantageously performed with certain additional details or refinements, which will be discussed shortly.

All of the foregoing operational principles and advantages of the present invention will be more fully appreciated upon consideration of the following detailed description, with reference to the appended drawings, of which:

BRIEF DESCRIPTION OF THE DRAWINGS

More specifically, FIGS. 1 and 2 show the trocar-inserting step numbered "1" in the preceding section of this document;

FIG. 3 shows the incision-making step numbered "2" in the preceding section;

FIGS. 4 through 6 show a preferred form of the trocar-tip-using step numbered "3" in the preceding section;

FIGS. 7 and 8 show the suture-installing step "4" as it would be performed in the absence of the maneuvering step "6"; and FIGS. 9 through 12 show the same suture-installing step "4" and the generally concurrent (or, more accurately, alternating) monitoring step "5" as these steps are performed in my invention in combination with the maneuvering step "6".

FIG. 7a is a body cross-sectional view, taken generally along the dogleg line 7a—7a in FIG. 7; but more accurately FIG. 7a is a composite view showing in a very schematic way the outermost extension of the bladder (which is actually behind the line 7a—7a in FIG. 7) and the entire embedded lengths of the suture-installing needles.

FIGS. 10a and 12a show the monitoring step "5" at the same stages as FIGS. 10 and 12 respectively. FIGS. 10a and 12a do include, for purposes of reference and comparison with FIGS. 7a through 9a, and FIG. 11a, the outermost extension of the bladder (which may in fact be slightly behind the viewing device, and in any event would not be viewable as a linear structure from within the bladder).

DETAILED DESCRIPTION OF THE PREFERRED EMBODIMENTS

Figure 1:
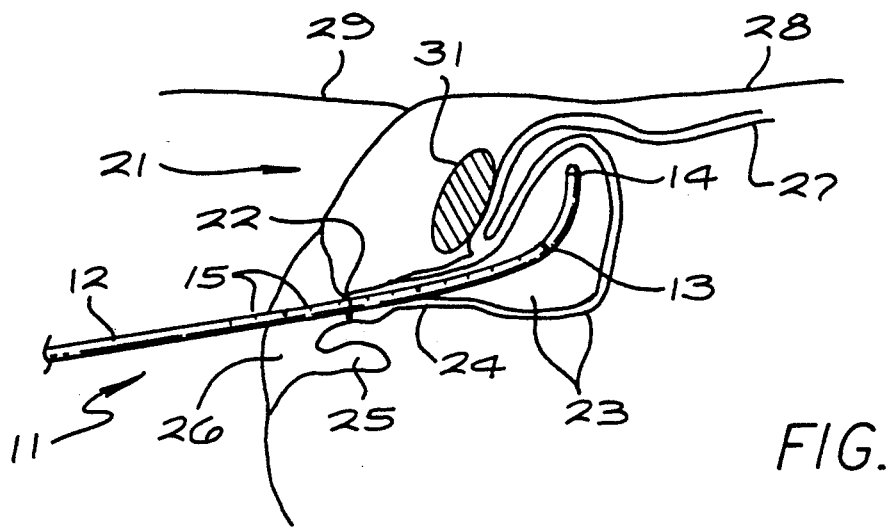
FIGS. 1 through 12 are generally diagrammatic fragmentary longitudinal sections, taken along the body midline of a representative supine patient, illustrating the successive steps of the procedure of my invention—both with and without the "maneuvering" step.

In FIG. 1 a trocar 11 is shown inserted into a patient's body 21. In the drawing, part of the shaft 12 of the trocar 11 lies within the patient's urethra 22, extending into the bladder 23 through the bladder neck or urethrabladder junction 24.

The trocar includes a curved shaft portion 13, which lies entirely or mostly within the bladder; and a shaped tip 14, which is within the bladder. Defined along the trocar shaft are indicia or graduations 15, to aid the operator in determining relative distances of insertion.

As is well known, the suspension procedure is intended to mitigate the inconveniences, embarrassments and discomfort of urinary incontinence that results from degeneration and sagging of the lower body-cavity wall. These conditions include sagging, some expansion or lateral stretching, and disorganized wrinkling or folding of the urethra 22 and bladder neck 24, together with a partial collapse of the neck 24 into the urethra 22. Under these conditions the urethral sphincter is unable to effect a well-defined closure of the urethra.

The drawing is intended to suggest these conditions. Also appearing in the drawing are the patient's vagina 25, perineum 26, peritoneum 27, external abdominal surface 28, and right leg 29.

Also well known is the general strategy of the suspension technique—namely, to employ the patient's vagina 25 essentially as a sling to lift the urethra upward and slightly forward (ventrally), toward the suprapubic portion of the abdomen. (Readers unfamiliar with this arrangement may refer ahead to FIGS. 8 and 8a, which generally illustrate the objecdtive of the overall procedure.) The result is to extend or erect the urethra 22, simultaneously narrowing it, and thereby to reposition and redefine the bladder neck 24.

Figure 2:
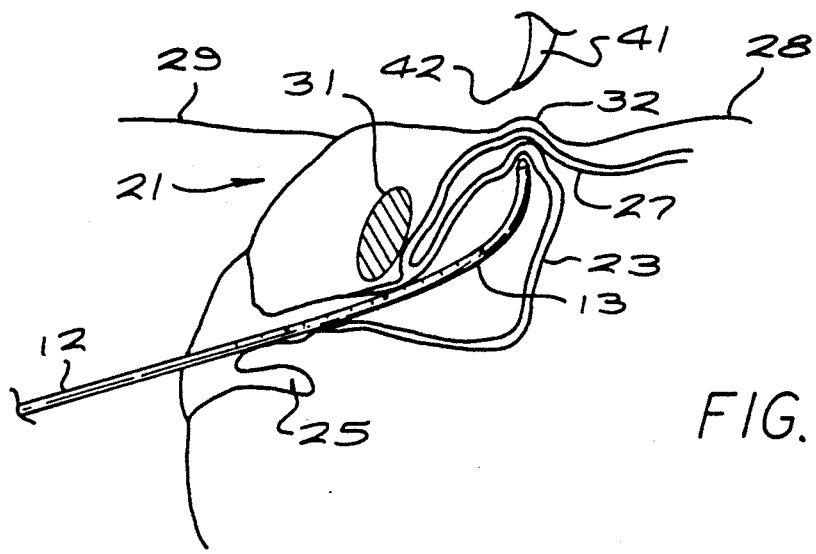

In FIG. 2 the trocar tip is advanced further—first against the bladder wall, and then yet further to press the bladder wall against the peritoneum 27. Further pressure causes displacement of both the peritoneum and exterior abdominal surface 28, visible at the outside of the patient's body as a distinct bulge 32 in the abdominal surface 28. FIGS. 1 and 2 thus represent the trocarinsertion step (1) mentioned in an earlier section of this document.

Figure 3:
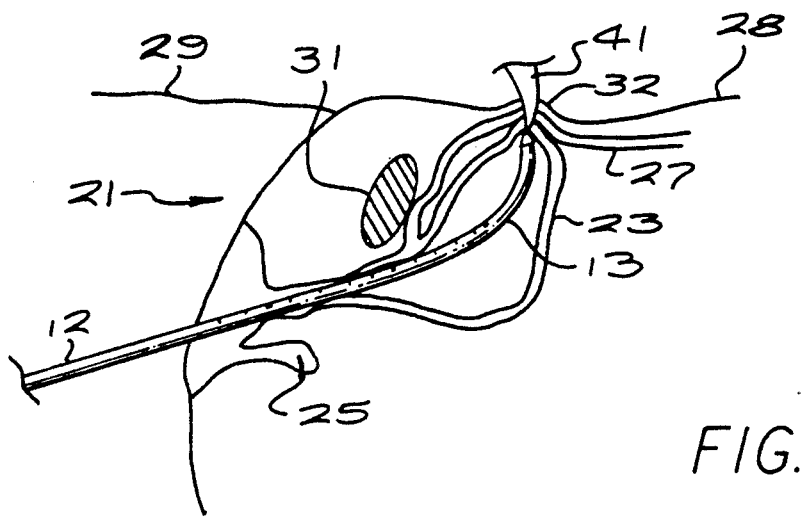

In FIGS. 2 and 3 a scalpel or like surgically sharp instrument 41 is advanced toward the bulge 32 from outside the patient's body, and carefully positioned so that a sharp tip 42 of the scalpel will meet the trocar tip 14. Then the operator pushes the scalpel tip 42 through the abdominal wall 28, peritoneum 27, and bladder wall 23, to engage the trocar tip 14.

FIG. 3 thus represents the incision-making step (2) stated earlier. As will be seen, to facilitate this step I prefer to form the trocar tip as a shallow recess or cup that positively receives the scalpel tip 42.

Figure 4:
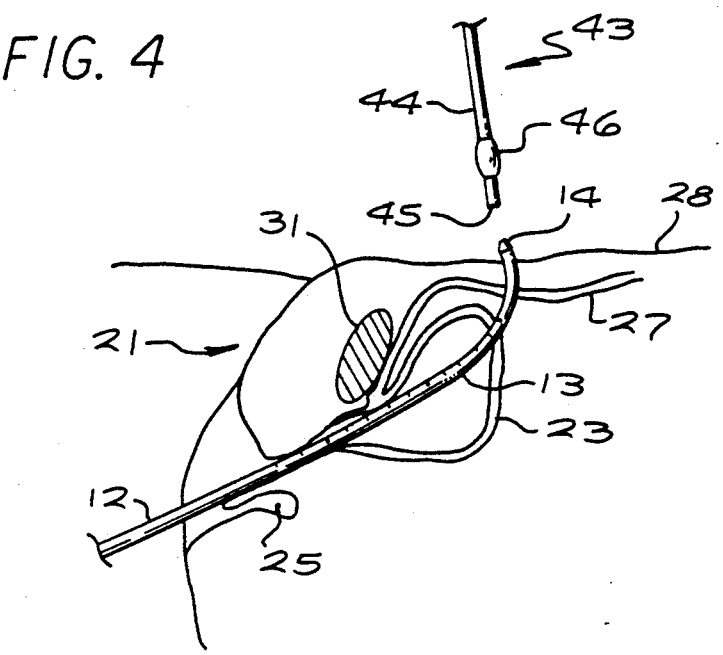

FIG. 4 shows that the trocar tip 14 can then be pushed outward through the incision just made, to protrude at the exterior of the patient's abdomen. In a preferred embodiment of my invention, a catheter 43 can then be positioned with its shaft 44 generally vertical above the abdomen and its tip 45 aligned with the trocar tip 14.

The catheter 43 is preferably of a type that includes an annular balloon 46 just behind the tip 45. This type of catheter also has an inflation lumen (not shown, but within the catheter shaft 44) for the balloon 46.

Figure 5:
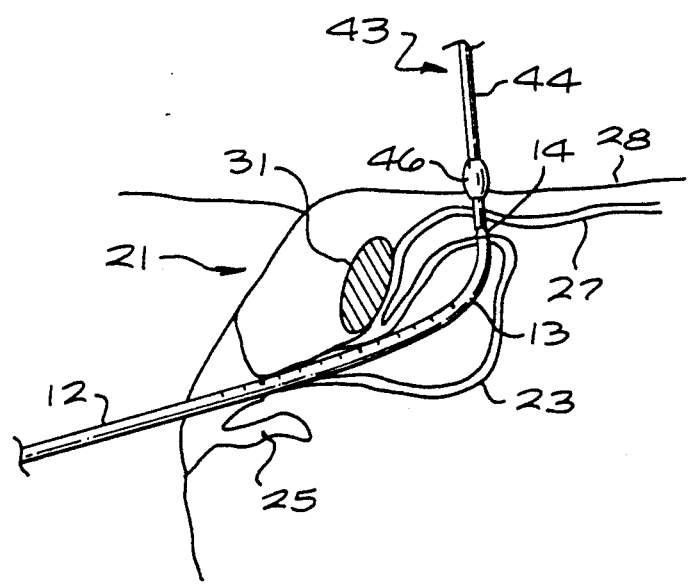

The operator firmly engages the catheter tip 45 with the trocar tip 14, by simply pushing them together; and then as shown in FIG. 5 the operator moves two tips, while continuing to hold them together, inward through the incision. The motion continues until the catheter tip 45 and the balloon 46, if present, are within the bladder.

Figure 6:
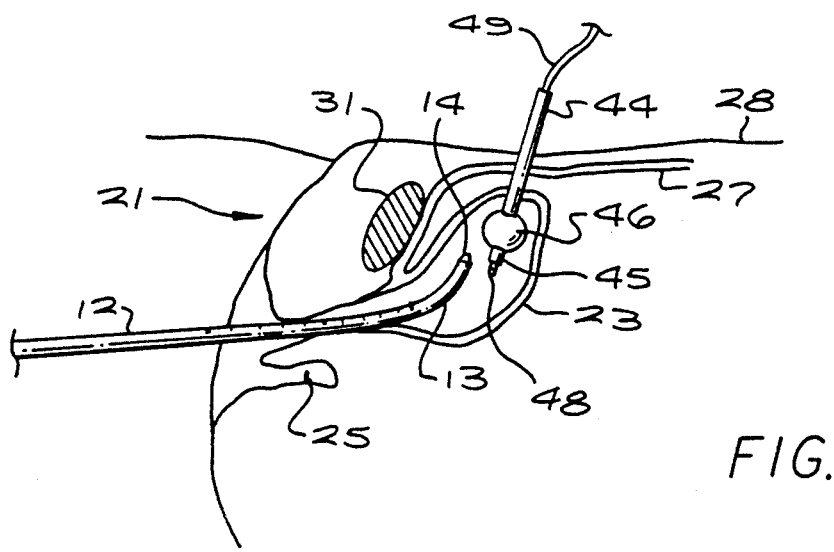

The catheter is preferably then anchored in this position—preferably by inflating a balloon 46 as shown in FIG. 6, but alternatively by sutures, adhesive, or other means.

A viewing device 48–49 is inserted through the catheter 44 and its tip 45, and into the bladder. The viewing device 48–49 can take any of a great number of forms—ranging, in principle, from a modified endoscope such as specified by Mason and Soderstrom in 1975, to a more modern ultrathin scanning optic-fiber unit that provides a viewable image only on a video screen, or perhaps a ureteroscope such as suggested very recently by Loughlin.

For present purposes the more modern viewing devices facilitate the procedure in the sense of minimizing the size of the required incision, and thereby slightly reducing the trauma to the patient; and also in the sense of making the image more readily visible to the person actually manipulating the trocar, etc.—as well as other medical personnel who may be involved. Nevertheless the procedure can be performed reliably, safely, and perhaps more economically (also thus slightly reducing trauma to the patient) with earlier 'scope-type viewers.

I prefer, as already indicated, to employ an embodiment of my invention that incorporates a catheter for establishment of the passage through the abdominal wall—and then to insert a viewing device through the catheter. I prefer this methodology because at least many viewing devices are relatively delicate and sensitive instruments, better not forced through a just-established incision. Moreover, a suprapubic drain catheter is highly desirable anyway, in or after the final stages of the procedure, to avoid complications that sometimes result from protracted use of a Foley urethral drain.

Nevertheless, the most basic function of the stages illustrated in FIGS. 4 through 6 is to insert and position the viewing device. Therefore, with respect to this function, the catheter 43 may be regarded as simply one form of intermediary appliance; or the movements shown may be considered as merely—in the words of the previously defined trocar-using step (3)—"using the tip of the trocar . . . indirectly to guide a tip of the viewing device through the suprapubic incision and into the woman's bladder".

FIGS. 4 through 6 thus represent that trocar-using step (3). It may now be appreciated why the term "indirectly" is included in the statement of that step.

As mentioned earlier, the trocar need not necessarily actually protrude fom the incision as shown in FIG. 4. If preferred, the catheter tip etc. may instead be mated with the trocar tip while the latter remains just within the incision, and then the two tips moved together into the bladder as in FIGS. 5 and 6. Such a variant is relatively awkward, and I do not prefer it; but I believe that it is encompassed within the scope of some embodiments of my present invention.

As described in my earlier patents on the suprapubic-incision procedure and instrument, using the trocar in the present procedure is very advantageous to identify the proper spot for the incision—and to minimize the likelihood of puncturing a bowel or other anomalously placed anatomical feature. In the present procedure, however, the coordinated use of the trocar and catheter etc. provide an important additional advantage: protecting against overinsertion of the catheter and viewing device.

For present purposes, the need for a clear view of the area where sutures may appear militates strongly against overinsertion of the viewing device. Insertion-distance graduations 15 (FIG. 1) on the trocar or catheter, or both, enhance this added advantage of the trocar system for forming the incision and installing the catheter and viewer.

The graduations, preferably with adjacent numerical distance indicia, are also useful in measuring the length of the urethra. This is possible in the present procedure because the practitioner can clearly see the markings inside the bladder and at the bladder neck, as well as outside the patient's body at the perineum. This feature can be used to help avoid overtightening the sutures, which otherwise may lead to various internal traumas as well as, in extreme cases, difficulty in urinating.

Figure 7:
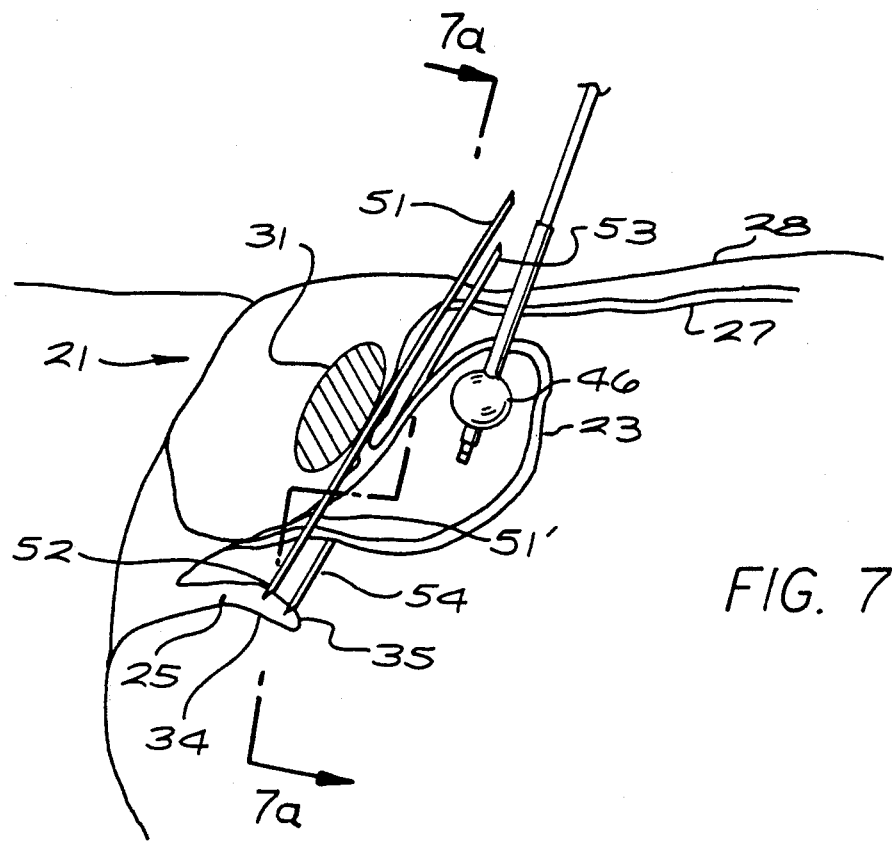
Figure 7A:
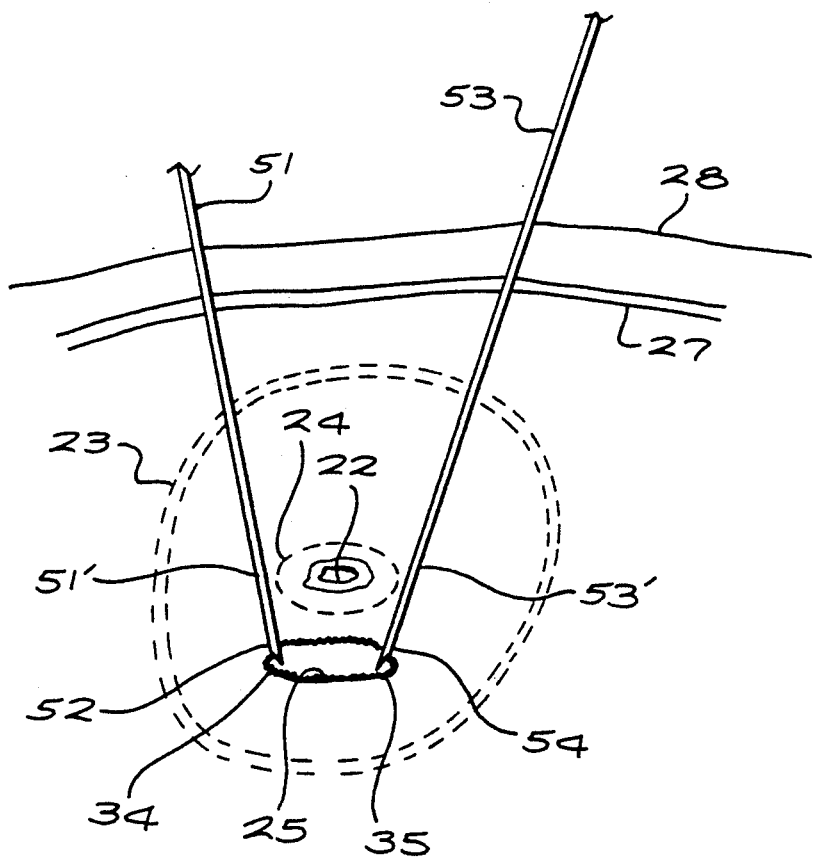
FIG. 7a shows the same stage of the suture-installing step "4" as FIG. 7, but from a different viewpoint. Very roughly speaking.

FIGS. 7 and 7a show in abbreviated form how the procedure would continue in the absence of the "maneuvering" step (6). These illustrations abbreviate the process in that they show two needles 51, 53 in use at once.

In actual practice, first a needle 51 would be used to install one suture just to the left of the urethra 22 and bladder neck 24, then the bladder would be filled for observation to determine whether the first suture was clear of the bladder and bladder neck, then the bladder would be emptied, next a needle 53 would be used to install another suture just to the right of the urethra 22 and bladder neck 24, then the bladder would be refilled to check the second suture, and finally the bladder would be reemptied.

Figure 8:
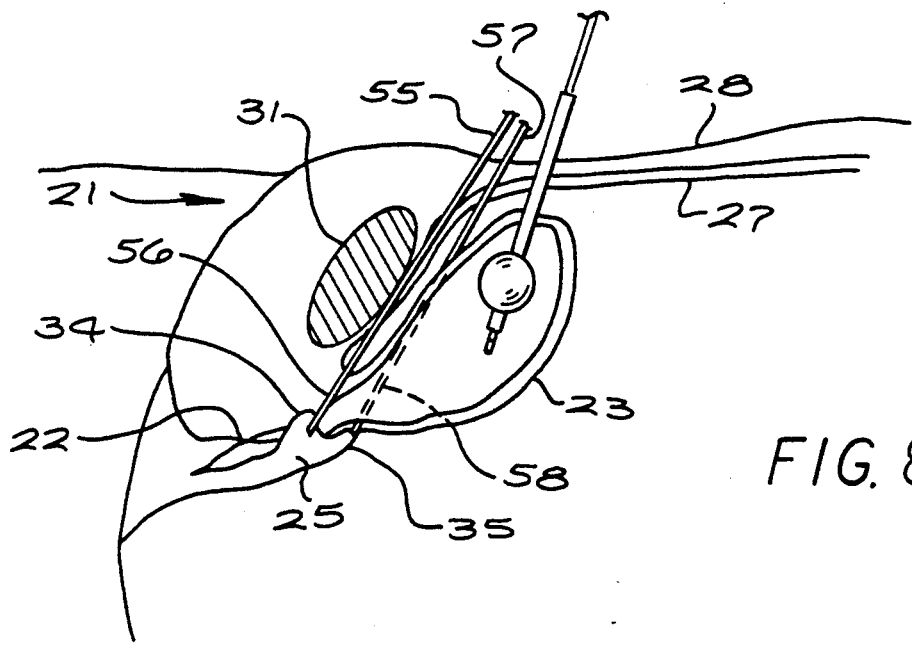
Figure 8A:
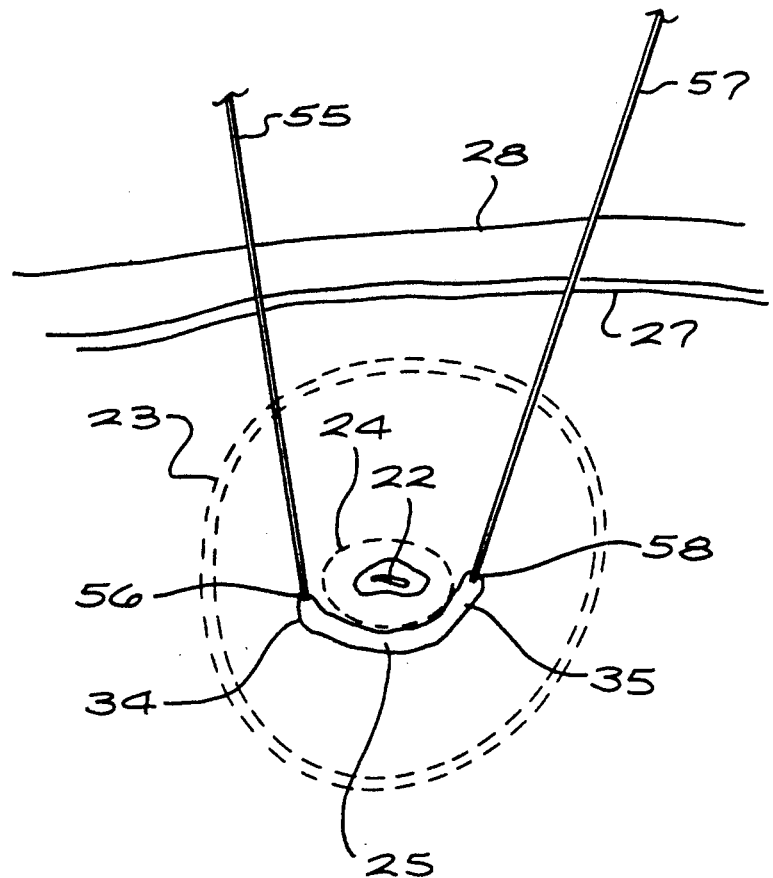
FIG. 8a in a similar very schematic and composite way shows the same stage of the suture-installing step "4" as FIG. 8.

That final step would be preparation for drawing up the two sutures 55, 57 as in FIGS. 8 and 8a. The latter two drawings show the ultimate objective of the overall procedure:

As can be seen, the left-hand suture 55, firmly secured at its terminus 56 to the vaginal wall near its left extremum 34, actually moves upward (that is, in the direction of the patient's head) and ventrally around the left side of the urethra 22 and bladder neck 24. Similarly the right-hand suture 57, secured at its terminus to the vaginal wall near its right extremum 35, moves upward and ventrally around the right side of the urethra 22 and bladder neck 24.

The vagina thus forms a suspension sling that lifts and extends the urethra 22 and neck portion 24 upward and ventrally, thereby narrowing the passageway and realigning it for control by the sphincter.

The bladder-filling steps mentioned above are desirable to facilitate observation, by unfolding and stretching the bladder wall to afford a better view of stray stitches—particularly those that may lie just below the mucous membrane that lines the bladder. The bladder-emptying steps are necessary because when the bladder is full it is larger and therefore much more difficult to avoid when passing the needles.

In conventional current practice the bladder is filled with water, although I consider that practice very undesirable because it takes much more time, degrades the optical conditions of observation, and adds to the patient's discomfort. In some cases the use of water may more readily produce inadvertent excessive inflation too, compromising the seal between the bladder wall and the catheter (or the viewing instrument directly)—and thereby leading to serious contamination of the peritoneal cavity.

FIGS. 7, 7a, 8 and 8a illustrate how closely the needles 51, 53 and sutures 55, 57 pass to the urethra 22 and bladder 23, and particularly to the bladder neck 24. From these views it can be understood how likely it is that sutures will pierce or at least graze into the wall of the bladder, the bladder neck, or even in unusual instances the urethra.

In particular, FIGS. 7 and 7a show that the left-side needle tip 52 passes—at generally the position marked 51'—immediately adjacent to the left side of the bladder neck 24. Any slight deviation of either the needle or the bladder neck can readily produce an intersection of the two.

Similarly, FIG. 7a shows that the right-side needle tip 54 passes—at generally the position marked 53'—immediately adjacent to the right side of the bladder neck 24. The vagina 25 is typically only slightly wider than, and not far behind, the bladder neck; and as already mentioned both features are usually in a deteriorated condition characterized by irregular or disorganized sagging, drooping and folding. In a typical case, therefore, the needle 51 or 53 on at least one side or the other is rather likely to graze the bladder neck 24.

Of course the observations conducted later are designed to detect and correct such accidents. Reliance upon such a quality-control approach, however, has two disadvantages.

First, correction (and consequent repetition of the observation steps) is time consuming. This effect increases not only the cost of the procedure but also the patient's discomfort, and for elderly patients may even degrade the prospects for recovery.

Second, the greater the percentage of sutures for which reliance is placed upon monitoring and correction, the greater the likelihood of overlooking and failing to correct a misplaced suture. A procedure that inherently limits the number of sutures requiring replacement is far preferable.

Figure 9:
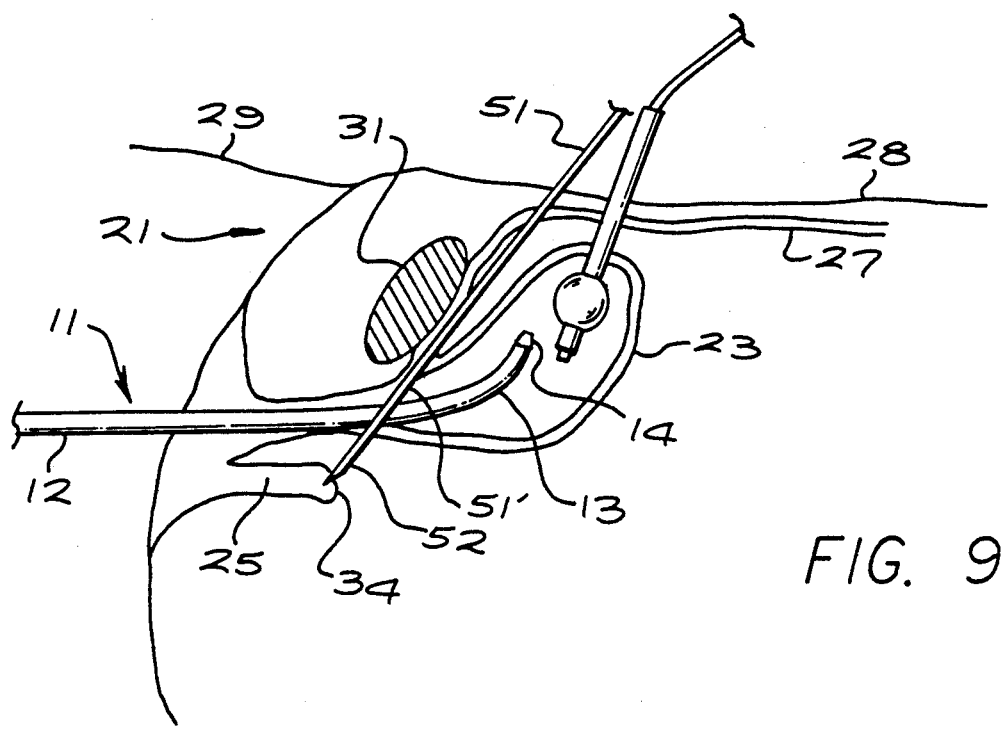
Figure 9A:
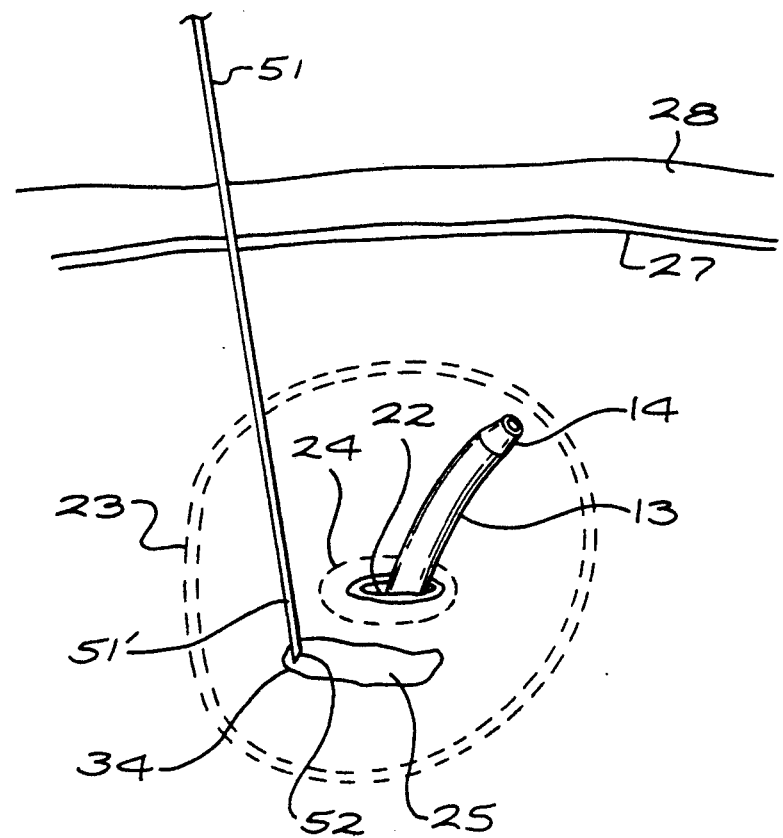
FIGS. 9a and 11a similarly shows the suture-installing step "4" at the same stages as FIGS. 9 and 11 respectively.

My present invention provides just such a procedure. As shown in FIGS. 9 and 9a, the trocar 11 remains in place during passing of the left-hand needle 51. As can be seen in FIG. 9a, the operator pushes the forward section 13 of the trocar toward the right, shifting rightward—and thus away from the needle path—the urethra 22, the bladder neck 24, and even to a slight extent the bladder wall 23.

Of course this shifting or deformation is initiated before passing the needle, and maintained during the needle passage. As a result the operator can gain significantly in clearance between the needle path and the critical region of the bladder neck.

A fair estimate or educated guess of the amount of clearance gained, in round numbers, is at least a centimeter and perhaps as much as two centimeters. As will be appreciated, however, the efficacy of this part of my procedure does not rely upon the precision of these estimates.

Figure 10:
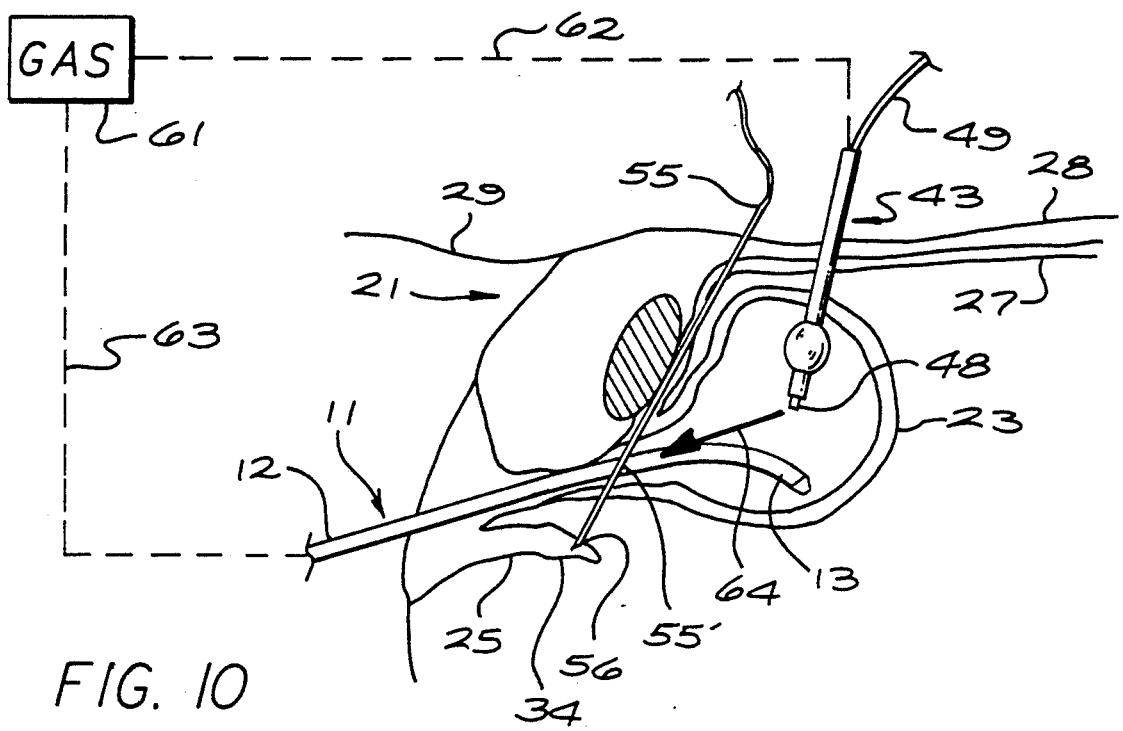
Figure 10A:
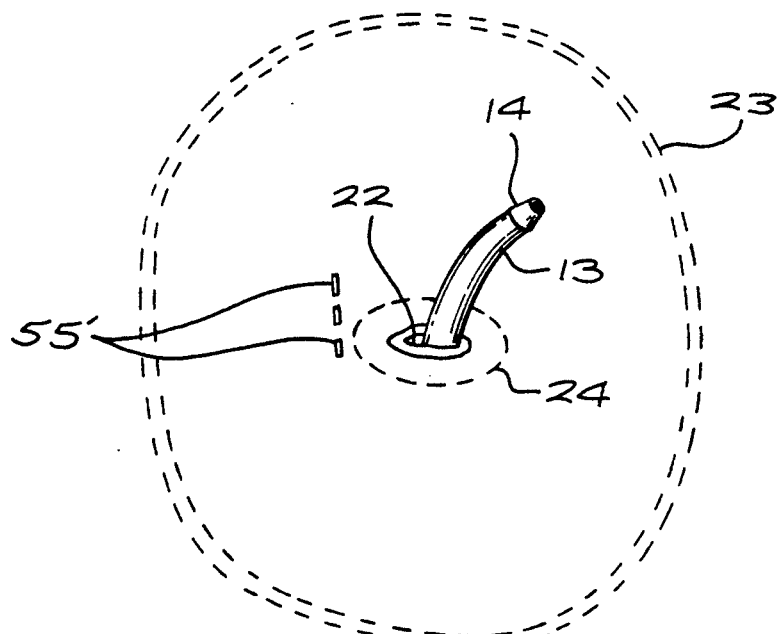
FIGS. 10a and 12a are not sectional views, but rather represent primarily actual viewable scenes as observed using a viewing device inserted through the suprapubic incision.

Following the installation of a left-side suture as in FIGS. 9 and 9a, the needle 51 is removed, and then the bladder should be obturated and the bladder neck inspected for misplaced sutures as illustrated in FIGS. 10 and 10a. I prefer obturation by means of gas, because of the increased speed, reduced weight and hence reduced discomfort, and better optical conditions. Because of the compressibility of gas, pressure also is applied in a gentler way, with a reduced likelihood of disturbing the seal made between the bladder wall 23 and the catheter or viewer. Where indicated, however, water obturation can of course be employed.

In either event the obturating medium (i.e., gas or water) can be supplied as from a source 61 through a conduit 62 or 63 to the catheter 43 or trocar 11, and therethrough to the bladder. When gas is preferred, of course the gas employued should be a relatively inert gas such as carbon dioxide. If preferred one of these tubular instruments can be used for introducing the medium into the bladder for each observation, and the other instrument for releasing the medium from the bladder after each observation.

Once the bladder has been expanded for observation, the viewing device 48-49 (and as appropriate the catheter 43) can be maneuvered to afford an optimum view toward the left side of the bladder neck, thus along a viewing direction—slightly out of the plane of the drawing—suggested by the arrow 64 in FIG. 10. This viewing direction is particularly ideal for seeing the left-side suture segment 55' of closest approach to the bladder neck 24, and to the nearby critical region of the bladder wall.

Accordingly as suggested in FIG. 10a any sutures 55' (shown in the broken line in FIG. 10a) that may be piercing or grazing the bladder neck or wall can be easily seen. Here too, if desired, the operator can press the forward trocar segment 13 to the right, as during the suture-placement step—to further mechanically stretch the neck and wall regions that are just to the left of the urethra, thereby adding to the tissue-flattening effects of the obturation for even better observation. In addition if desired the trocar can be rotated as suggested in FIG. 10 to move the curved segment 13 and tip 14 more conveniently away from the visual-field portion of greatest interest.

I wish to emphasize that the "maneuvering" step illustrated in FIGS. 9 and 9a minimizes the likelihood of sutures piercing or grazing the bladder wall or neck, and therefore that in my procedure the likelihood is very small that a suture will actually be seen at 55' as shown in FIG. 10a. This drawing therefore illustrates what is in my procedure a relatively very unusual case, though I believe it to be a much more likely case in earlier procedures.

Figure 11:
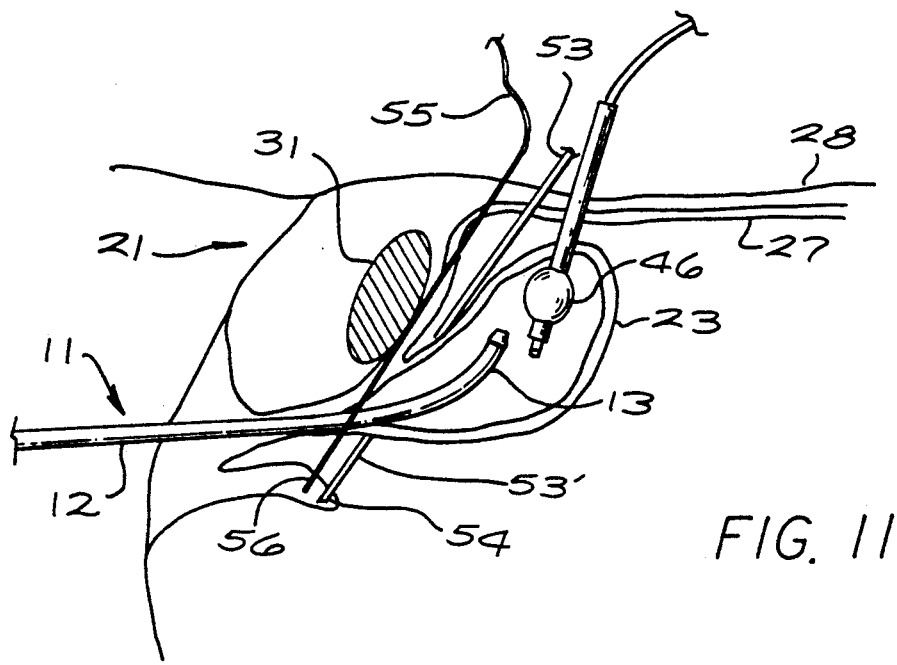
Figure 11A:
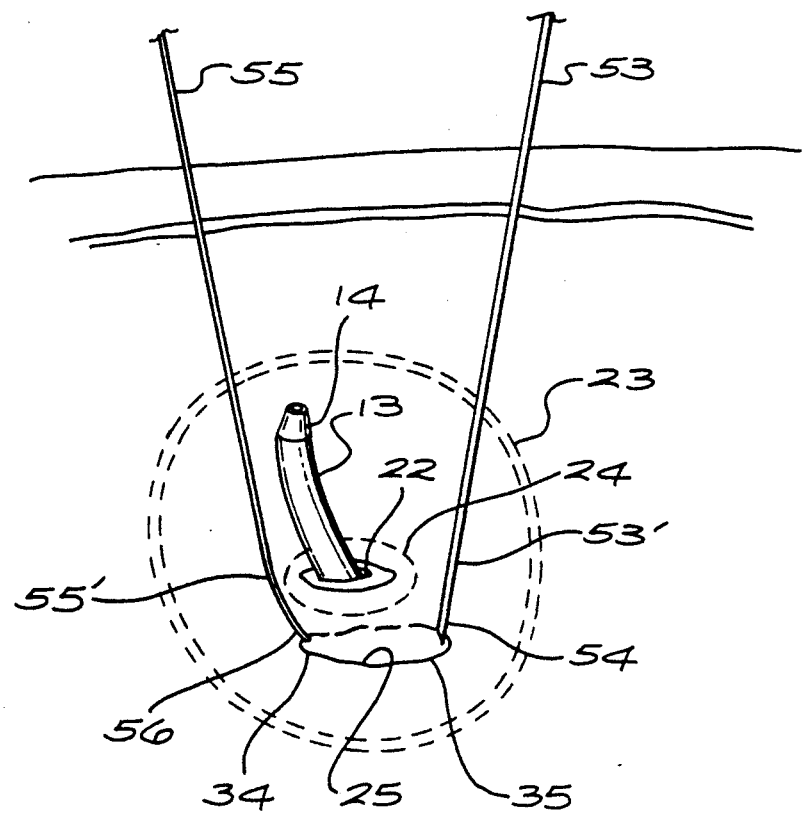

After the observation of FIGS. 10 and 10a, the obturating medium is removed—which is to say, the bladder is deflated. Then, as shown in FIGS. 11 and 11a, a second needle 53 is used to install a suture to the right side of the bladder, neck and urethra.

In this case the trocar curved segment 13 is pushed laterally to the left, drawing the tissues in that direction and thus moving the urethra 22, the bladder neck 24, and to some slight extent the bladder wall 23, away from the needle path. Once again, I estimate that clearance added by this simple effort is probably in the range of one to two centimeters.

Of course the movement of these features to the left brings them closer to the left-side suture 55, at its closest-approach point 55'—but that suture is already installed and is slack, and the installing needle preferably is already removed. Under these conditions the left side of the bladder neck may be pressed even directly against the left-side suture 55, 55' without creating any hazard.

Figure 12:
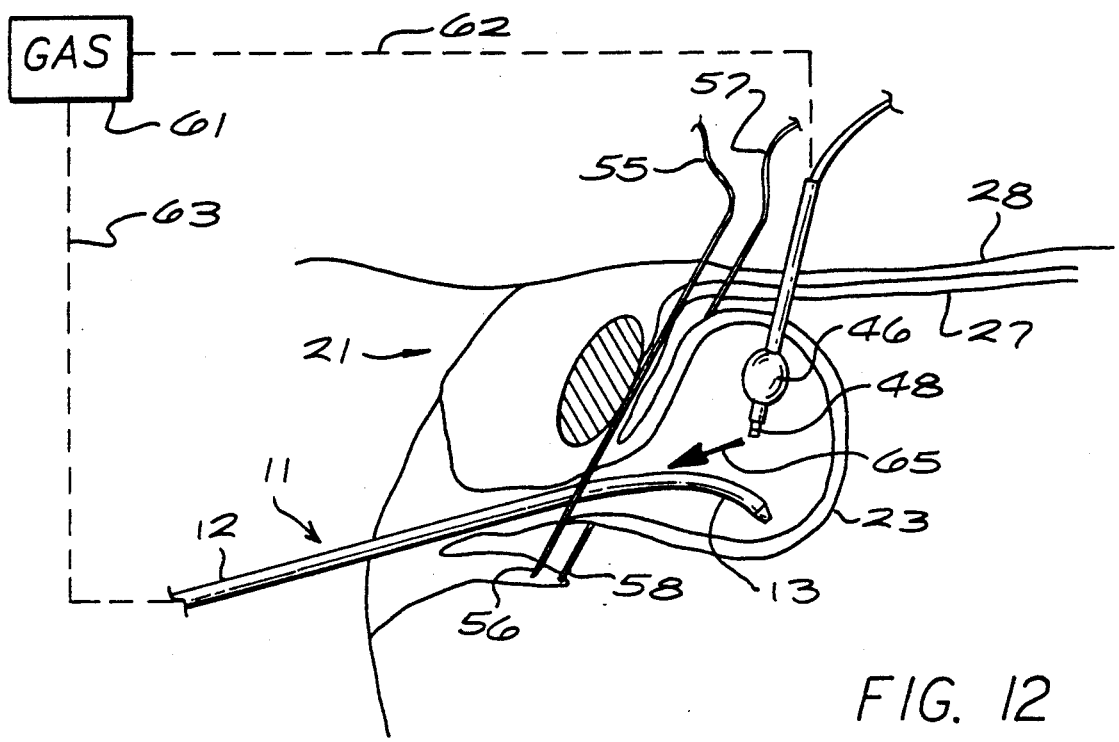

The right-side needle 53 is then removed, leaving the suture 57 in place, and the bladder is obturated once again—as shown in FIG. 12. Here the viewing device 48 may be disposed for an optimum view of the right side of the bladder neck and adjacent bladder wall, along the viewing direction suggested by the arrow 65 in FIG. 12; and if desired for a clearer view the trocar may be rotated away from the right side visual-field portions of interest.

As before, because of the maneuvering illustrated in FIGS. 11 and 11a, it will be unlikely that a suture will have been placed in the bladder neck or wall. If a suture has been so placed, however, it will be readily visible—as in the broken line 57' (in FIG. 12a)—by means of the viewing device, positioned at the opposite side of the bladder. Here too, the trocar curved segment 13 can be shifted to the left, to aid in stretching the tissues at the right—to add to the effects of the obturation and thereby provide an even better view of the right-side critical region.

FIGS. 9 through 12, and 9a through 12a, thus in the aggregate represent the installing, monitoring, and maneuvering steps (4) through (6) of my procedure. More specifically, FIGS. 9, 9a, 11 and 11a show iterations of the installing and maneuvering steps (4) and (6); while FIGS. 10, 10a, 12 and 12a show iterations of the monitoring steps (5).

Figure 12A:
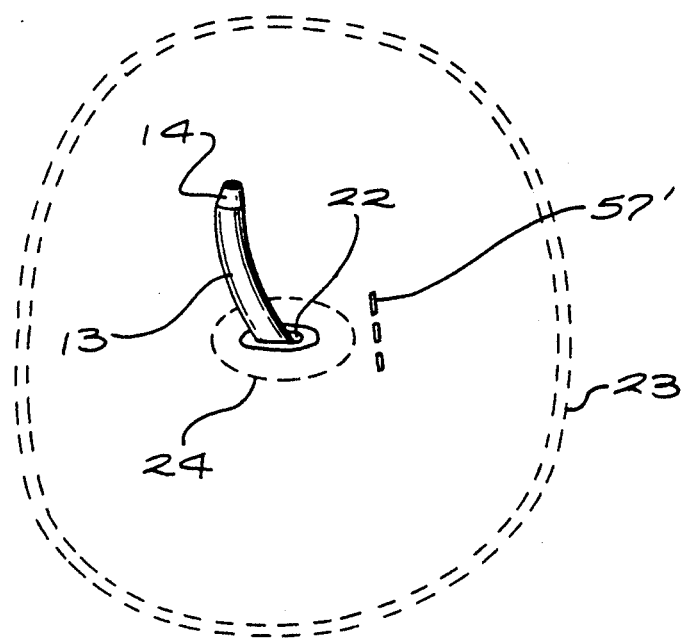

If a suture can be seen in the view of either FIG. 10a or FIG. 12a, of course it must be released and replaced correctly. When both sutures are correctly installed, the procedure is complete—and the result should be generally as illustrated in FIGS. 8 and 8a.

The precise techniques and manipulations directly involved in the actual placement of sutures, particularly such details as double passing through the vaginal wall, are outside the scope of this document and are generally performed as described in the technical papers mentioned earlier. The content of those papers is incorporated by reference—as are the content of my earlier patents directed to details of the suprapubic incision, movement of an instrument through that incision into the bladder, etc.; and the content of my earlier patent directed to practical details of gas obturation.

Figure 13:
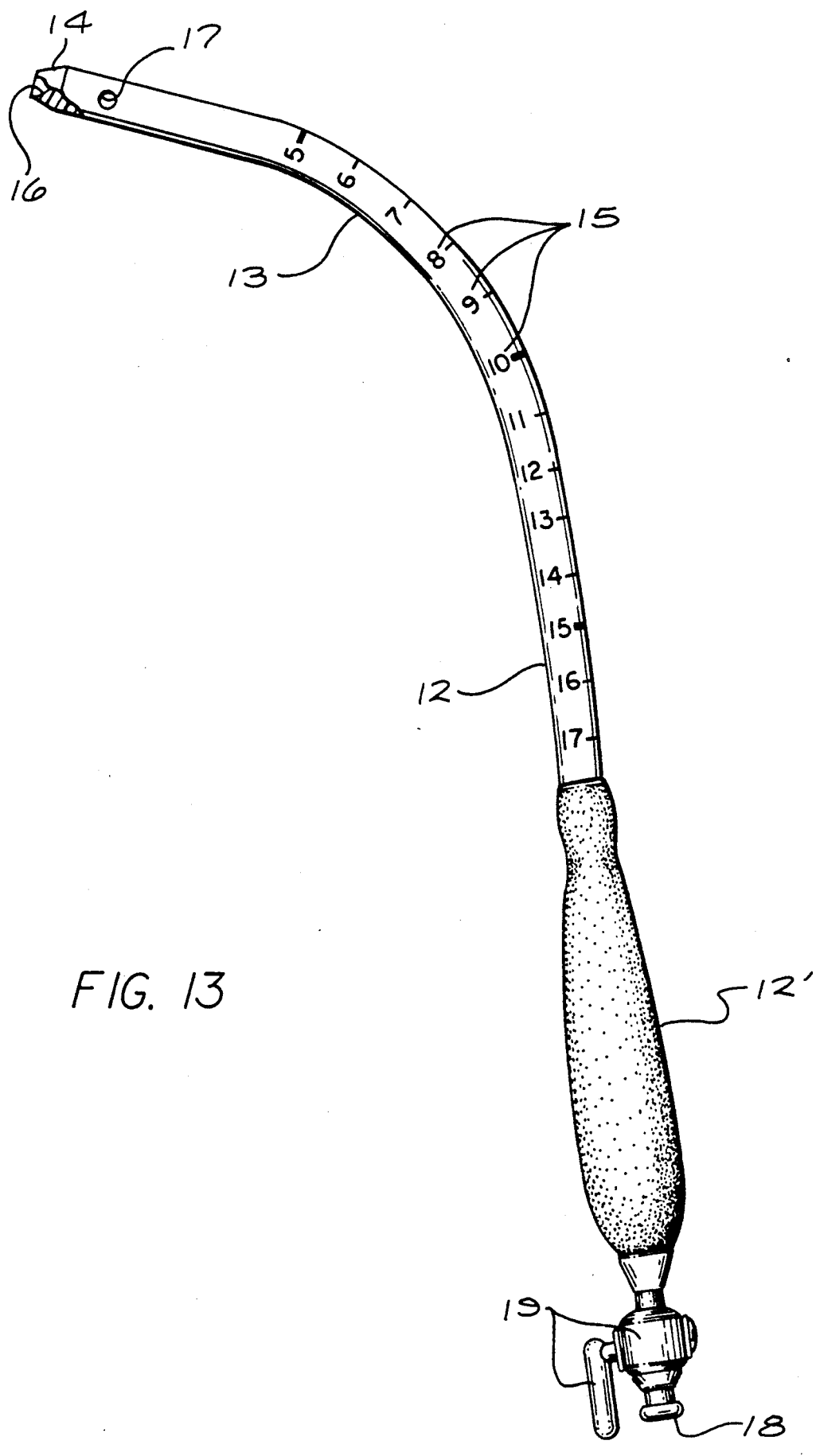
FIG. 13 is an external elevation, partly broken away to show a fragmentary cross-section, of a trocar particularly suited for use in practice of the procedure.

FIG. 13 shows that the trocar used in my procedure advantageously has, formed in its tip, a concave depression 16. This shallow cup or recess 16 receives the pointed tip 42 of the scalpel 41 (FIGS. 2 and 3) and later the tip 45 of the catheter 43 (FIGS. 4 through 6)—or other intermediary appliance, or the viewing device 48-49 directly if no intermediary is in use.

This configuration is thus a modification of the trocar geometries disclosed in my earlier patents relating to installation of a suprapubic catheter. Based upon my intervening experience, I believe that the configuration shown in FIG. 13 offers a significant improvement in simplicity.

The trocar configurations of my two earlier patents both incorporate a removable blunt convex tip which is used at the outset to engage the scalpel tip, and immediately thereafter during the process of passing the trocar outward through the incision. Once it is protruding from the incision, the tip is unscrewed for access to the connection device—either a socket, as in my '281 patent, or a hook as in my '486 patent—for engagement with a catheter.

The configuration of FIG. 13 eliminates the need to unscrew any removable tip. In using either earlier design, occasionally the removable tip can be overtightened before insertion, leading to some slight patient discomfort as force is later applied to unscrew it.

In addition the present configuration removes the alternative hazard, however theoretical and remote it may be, of initially inserting the trocar with the tip slightly loose—and then having it fall off within the patient's bladder. The FIG. 13 tip configuration is also slightly more economical to manufacture.

Despite these improvements, the FIG. 13 configuration functions almost identically with the trocar of my '281 patent, in engaging the tip of the catheter or other device for passage through the incision and into the bladder. With the present configuration, in other words, the tip of the catheter etc. is simply pressed and held into the cup 16. As to comparison with the trocar of my '486 patent, the function of the present configuration appears to be a clear improvement for a vaginal-suspension procedure, for the following reasons.

In the present procedure, the trocar remains in the bladder for an extended period after formation of the incision and is maneuvered within the bladder for the purposes explained above. Because of this extended use, the hooked-tip configuration disclosed in my '486 patent may be somewhat undesirable, as it may present some slight potential for inadvertent trauma to the interior of the bladder wall during the maneuvering.

In addition, as compared with the hooked-tip design, the present configuration is much improved in ease of disconnection of the trocar from the catheter tip once the latter has been moved into the bladder. For some operators a certain amount of practice may be needed to unhook the two tips, when they are both out of view within a patient's bladder.

Finally, the hooked-tip design works best with a customized matching eyelet or the like at the tip of the catheter or other intermediary appliance, or at the tip of the viewing device if no intermediary is in use. Accordingly the configuration shown in FIG. 13 may offer some reduction in the need for specialized equipment, for performance of the procedure of the present invention.

Nevertheless my two earlier trocar configurations have both been proven serviceable, and either may be employed in the present procedure satisfactorily with proper precautions as suggested above.

In addition to the recess 16 shown in FIG. 13 and just discussed, I prefer for present purposes to define length indicia 15 along the shaft 12-13 of the trocar. These markings may include, for example, centimeter graduations as illustrated—together with, preferably, numerals indicating the number of centimeters along the shaft from the tip 14. These various indicia 15 may be etched or stamped into the trocar surface, or otherwise suitably applied—with due attention to avoiding contamination of the patient's system.

As described in my earlier patents the trocar is advantageously formed with a lumen extending from a lateral aperture 17 near the tip 14 through the entire length of the trocar to a suitable hose fitting or the like 18 at or near the opposite end. A valve 19 may also be included, or may be supplied in the external plumbing (not illustrated) to which the fitting 18 will be attached.

The lumen 17-18 may be used for initial draining of the bladder, or for preliminary irrigation thereafter, or for obturation with either gas or liquid, or for combinations of any of these or other functions. The shaft 12 preferably is fitted with a soft elastomeric handgrip 12' to afford the operator a secure grasp of the instrument.

It will be understood that the foregoing disclosure is intended to be merely exemplary, and not to limit the scope of the invention—which is to be determined by reference to the appended claims.

I claim:

1. A procedure for treating incontinence in a woman, comprising the steps of:
   inserting a urethral trocar into the woman's bladder and therethrough to press outward firmly against the woman's abdominal wall, so as to be perceptible from the exterior of the woman's body;
   then, with the exteriorly perceptible trocar as a guide, making a suprapubic incision in the woman's abdominal wall and bladder to gain access to a tip of the trocar;
   then using the tip of the trocar directly or indirectly to guide a tip of a viewing device through the suprapubic incision and into the woman's bladder; and
   then installing sutures between the woman's rectus fascia and vagina, by means of a needle inserted through the woman's abdomen and into the woman's vagina;
   substantially during the suture-installing step, monitoring the interior of the bladder through the viewing device to avoid placement of sutures in the bladder wall;
   whereby the viewing device is remote from the neck of the bladder, where inadvertent placement of sutures is particularly likely; and
   substantially during the suture-installing and monitoring steps, maneuvering the trocar or the viewing device, or both, to manipulate tissues of the woman's bladder, urethra, or abdominal wall, or combinations of any of these tissues, to facilitate accurate placement of the sutures, particularly avoiding the bladder and urethra.

2. The procedure of claim 1, wherein the tip-using step comprises the substeps of:
   employing the tip of the trocar directly or indirectly to guide an end of a catheter through the suprapubic incision into the woman's bladder; and
   then inserting the tip of the viewing device through the catheter into the woman's bladder.

3. The procedure of claim 2, further comprising:
   after the suture-installing step, withdrawing the viewing device and leaving the catheter in place for drainage of urine from the bladder until the woman recovers from immediate effects of previous steps.

4. The procedure of claim 2, wherein the trocar-tip-employing substep comprises:
   mating the end of the catheter or an intermediary appliance with the tip of the trocar; and
   then moving the end of the catheter or appliance, while it is mated with the tip of the trocar, inward through the incision and into the woman's bladder.

5. The procedure of claim 2, wherein the trocar-tip-employing substep comprises:
   passing the trocar tip outward through the suprapubic incision;
   then mating the tip of the catheter or of an intermediary appliance with the tip of the trocar; and
   then moving the tip of the catheter or appliance, together with the tip of the trocar, inward through the incision and into the woman's bladder.

6. The procedure of claim 2, wherein:
   the monitoring step comprises inflating the bladder with gas through the catheter, viewing device, or trocar, or combinations of these paths.

7. The procedure of claim 1, wherein the tip-using step comprises the substeps of:
   providing a catheter that has near its end a balloon;
   employing the tip of the trocar directly or indirectly to guide the end of the catheter and the balloon through the suprapubic incision into the woman's bladder;
   inflating the balloon to anchor the end of the catheter within the bladder; and
   after the employing substep, inserting the tip of the viewing device through the catheter into the woman's bladder.

8. The procedure of claim 7, further comprising:
   after the suture-installing step, withdrawing the viewing device and leaving the catheter anchored in place by the balloon for drainage of urine from the bladder until the woman recovers from immediate effects of the previous steps.

9. The procedure of claim 1, wherein the trocar-tip-using step comprises:
   mating the tip of the viewing device or of an intermediary appliance with the tip of the trocar; and
   then moving the tip of the viewing device or appliance, while it is mated with the tip of the trocar, inward through the incision and into the woman's bladder.

10. The procedure of claim 1, wherein the trocar-tip-using step comprises:
    passing the trocar tip outward through the suprapubic incision;
    then mating the tip of an viewing device or of an intermediary appliance with the tip of the trocar; and
    then moving the tip of the viewing device or appliance, together with the tip of the trocar, inward through the incision and into the woman's bladder.

11. The procedure of claim 1, further comprising:
    before the inserting step, making or obtaining a urethral trocar that bears visible graduations along at least part of its length;
    wherein the trocar-maneuvering step comprises referring to the graduations as they appear at the woman's perineum.

12. The procedure of claim 1, wherein:
    the monitoring step comprises inflating the bladder with gas.

13. The procedure of claim 1, wherein the installing and monitoring steps comprise repetitive performance of this sequence of substeps:
    placing a suture;
    then inflating the bladder with gas to facilitate observation of the bladder wall;
    then observing the bladder wall to determine whether the suture just placed is visible therein; and
    then deflating the bladder.

14. The procedure of claim 13, wherein:
    the inflation and deflation substeps are performed by passage of gas through the trocar or viewing device, or both.

15. The procedure of claim 1, further comprising the step of:
    before the inserting step, making or obtaining a urethral trocar with a recess at its tip and a generally peripheral ridge around the recess;
    wherein the incision-making step comprises pressing a sharp object through the abdominal wall and bladder, and toward and into the recess.

16. The procedure of claim 1, further comprising the step of:
    before the inserting step, making or obtaining a urethral trocar with a recess at its tip and a generally peripheral ridge around the recess, and that bears visible graduations along at least part of its length;
    wherein the incision-making and trocar-using steps comprise referring to the graduations as they appear at the woman's perineum, to aid in positioning the trocar; and
    wherein the incision-making step comprises pressing a sharp object through the abdominal wall and bladder, and toward and into the recess.

17. A procedure for treating incontinence in a woman, comprising the steps of:
    inserting a urethral trocar into the woman's bladder and therethrough to press outward firmly against the woman's abdominal wall, so as to be perceptible from the exterior of the woman's body;
    then, with the exteriorly perceptible trocar as a guide, making a suprapubic incision in the woman's abdominal wall and bladder to gain access to a tip of the trocar;
    providing a catheter that has near its end a balloon;
    then mating the end of the catheter or an intermediary appliance with the tip of the trocar; and
    then moving the end of the catheter or appliance, while it is mated with the tip of the trocar, inward through the suprapubic incision and into the woman's bladder;
    then positioning the balloon within the woman's bladder;
    then inflating the balloon to anchor the end of the catheter within the bladder; and after the moving step, inserting the tip of a viewing device through the catheter into the woman's bladder;

whereby the viewing device is remote from the neck of the bladder, where inadvertent placement of sutures is particularly likely;

then installing sutures between the woman's rectus fascia and vagina, by means of a needle inserted through the woman's abdomen and into the woman's vagina;

substantially during the suture-installing step, monitoring the interior of the bladder through the viewing device to avoid placement of sutures in the bladder wall;

the installing and monitoring steps comprising repetitive performance of this sequence of substeps: (1) placing a suture, then (2) inflating the bladder with gas through the catheter, viewing device, or trocar, or combinations thereof, to facilitate observation of the bladder wall, then (3) observing the bladder wall to determine whether the suture just placed is visible therein, and then (4) deflating the bladder through the catheter, viewing device, or trocar, or combinations thereof;

substantially during the suture-installing and monitoring steps, maneuvering the trocar or the viewing device, or both, to manipulate tissues of the woman's bladder, urethra, or abdominal wall, or combinations of any of these tissues, to facilitate accurate placement of the sutures, particularly avoiding the bladder and urethra; and after the suture-installing step, withdrawing the viewing device and leaving the catheter anchored in place by the balloon for drainage of urine from the bladder until the woman recovers from immediate effects of the previous steps.

18. The procedure of claim 17, further comprising the step of:

before the inserting step, making or obtaining a urethral trocar that bears visible graduations along at least part of its length;

wherein the trocar-maneuvering step comprises referring to the graduations as they appear at the woman's perineum.

19. The procedure of claim 17, further comprising the step of:

before the inserting step, making or obtaining a urethral trocar that bears visible graduations along at least part of its length, and that has a recess at its tip and a generally peripheral ridge around the recess;

wherein the incision-making step comprises pressing a sharp object inward through the abdominal wall and bladder, and toward and into the recess; and wherein the trocar-maneuvering step comprises referring to the graduations as they appear at the woman's perineum.

* * * * *